United States Patent [19]

Nathanson

[11] Patent Number: 4,783,457

[45] Date of Patent: Nov. 8, 1988

[54] PEST CONTROLLING AGENTS

[75] Inventor: James A. Nathanson, Wellesley, Mass.

[73] Assignee: The General Hospital Corporation, Boston, Mass.

[21] Appl. No.: 26,968

[22] Filed: Mar. 17, 1987

Related U.S. Application Data

[63] Continuation of Ser. No. 605,847, May 1, 1984, Pat. No. 4,678,775.

[51] Int. Cl.$^4$ .............. A01N 43/84; A01N 43/54; A01N 43/78; A01N 43/76

[52] U.S. Cl. .............. 514/227.2; 514/256; 514/365; 514/374; 514/377; 514/401; 514/426; 514/638; 514/653; 514/228.8

[58] Field of Search .............. 514/183, 222, 254, 256, 514/263, 370, 396, 398, 404, 637, 653, 677, 365, 374, 377, 426, 638

[56] References Cited

U.S. PATENT DOCUMENTS

| | | | |
|---|---|---|---|
| 4,118,508 | 10/1978 | Bhat et al. | 514/455 |
| 4,134,986 | 1/1979 | Bajwa | 514/455 |
| 4,302,457 | 11/1981 | Voorhees et al. | 514/269 |
| 4,342,585 | 8/1982 | Motomura et al. | 71/88 |

OTHER PUBLICATIONS

Nathanson et al., Mol. Pharm. 20:68–75, 1981.
Chang et al., J. Agri. Food Chem., 25:493–501.
Seaman et al., J. Med. Chem. 26:436–439, 1983.
Hollingworth et al., Science 208:74–76, 1980.
Evans Nature, 287:60–62, 1980.
Nathanson et al., Science, 180:308–310, 1973.
Nathanson et al., Science, 203:65–68, 1979.

*Primary Examiner*—John Rollins
*Attorney, Agent, or Firm*—Saidman, Sterne, Kessler & Goldstein

[57] ABSTRACT

The invention relates to an invertebrate pest controlling composition comprising an invertebrate pest-controlling amount of a non-formamidine octopamine against having substantial activity toward an octopamine receptor present in an invertebrate pest and a pesticidally inert carrier.

7 Claims, 5 Drawing Sheets

PEST CONTROLLING AGENTS

This application is a continuation of application Ser. No. 605,847, filed May 1, 1984, now U.S. Pat. No. 4,678,775.

BACKGROUND OF THE INVENTION

1. Field of the Invention

The present invention relates to pest controlling agents having pest controlling activity and to methods of controlling pests by treatment with the aforementioned agents.

2. Description of the Background Art

Despite the recent development and great promise of such advanced pest controlling compositions as chemical sterilants, pheromones or ecologically-based insect control strategies, it is doubtless that, at present, the use of chemical pesticides still plays a predominant role. The use of insecticides often represents the difference between profitable crop production for farmers and no marketable crop at all, and the value of insecticides in controlling human and animal diseases has been dramatic.

Therefore, in parallel to the aforementioned newer technologies for pest control, there has been active research and investigation into the detailed biochemical modes of action of existing known chemical pesticides. Thus, for example, Nathanson et al., *Molecular Pharmacology* 20: 68–75 (1981) presented evidence indicating that the formamidine pesticides chlordimeform (CDM) and N-demethylchlordimeform (DCDM) may affect octopaminergic neurotransmission. CDM and DCDM have been reported to mimic the effects of octopamine in stimulating light emission in the firefly lantern (Hollingworth, R. M. et al., *Science*, 208: 74–76 (1980)), and in effecting nerve-evoked muscle responses in the locust leg (Evans, P. D., *Nature*, 287: 60–62 (1980)). Nathanson et al., supra, found that DCDM, which is the probable in vivo metabolite of CDM, is about six-fold more potent than octopamine itself as a partial agonist of light organ octopamine-stimulated adenylate cyclase. Stimulation by the formamidines resulted in increased formation of the intracellular messenger, cyclic AMP. This stimulation was blocked by cyproheptadine, clozapine, fluphenazine and phentolamine compounds, also known to block the octopamine receptor. Nathanson et al. concluded that DCDM is the most potent octopaminergic compound described.

Similar results were observed by Hollingworth et al. (reported in the Scientific Papers of the Institute of Organic and Physical Chemistry of Wroclaw Technical University, No. 22, Conference 7 (1980)). These authors demonstrated that certain formamidines act on octopamine receptors to induce the synthesis of cyclic AMP, and that this response is blocked by both phentolamine and cyproheptadine, which are known to act as octopaminergic antagonists in insects. The authors also suggested that these formamidines are potent stimulators of the octopamine sensitive adenylate cyclases in the thoracic ganglia of *Periplaneta americana*, and in the ventral nerve cord and fat body of *M. sexta*. The authors suggest that the stimulation of octopamine receptors underlies a number of toxic responses seen with formamidines on insects.

It should be noted that the presence of an insect adenylate cyclase enzyme which is sensitive to naturally occurring D(−) octopamine as a "neuro transmitter" has been known for some time (Nathanson et al, *Science*, 180: 308–310 (1973) (cockroach); Nathanson, ibid: 203: 65–68 (1979) (firefly); Evans, J., *Neurochem*, 30: 1015–1022 (1978) (cockroach)).

The study of cyclic AMP (cAMP) as a "second messenger" has led to the accepted model that a hormone or neurotransmitter binds at a cell-membrane bound receptor, which activates adenylate cyclase to a form capable of converting ATP in the cytoplasm of the cell into cAMP. cAMP then relays the signal brought by the hormone or neurotransmitter from the membrane to the interior of the cell. Agonists of the hormone or neurotransmitter are, by definition, capable of eliciting the same response (see, for example, Nathanson and Greengard, *Scientific American*, 237: 108–119 (1977)). Once formed inside the cell, cyclic AMP presumably binds to a protein kinase which is then capable of phosphorylating appropriate proteins, etc.

Given the continuous need for increased selectivity and effectiveness in pest control agents, it became desirable that the greater understanding of the biochemical mode of action of the formamidines be utilizable in some manner to lead to a general rational formulation of pest control agents.

SUMMARY OF THE INVENTION

The present invention arose out of the initial observations by the inventor and others that the mode of action of certain formamidine pesticides was through their octopaminergic agonist activity on octopamine receptors present in the pest, and that these pest control agents were acting through generation of cAMP as a "second messenger." It was not clear at the time of these observations whether these were generalizable observations or were isolated instances. The inventor has now observed that other, non-formamidine octopaminergic agonists are also pest control agents. In fact, the inventor's observations have extended beyond the octopaminergic agonists to compounds that directly effect adenylate cyclase and, further, to cAMP analogues. Thus, in one embodiment, the present invention provides a pest controlling composition which comprises:

a compound having pest-controlling activity towards said pest, selected from the group consisting of
 (1) a non-formamidine octopamine agonist toward an octopamine receptor present in said pest;
 (2) a compound directly stimulating the enzyme adenylate cyclase; and
 (3) a cyclic adenosine monophosphate (cAMP) analogue.

FIG. 8 indicates the three types of pest control agents having pest control activity useful in this invention. These are either non formamidine octopamine agonists (1), direct adenylate cyclase enzyme stimulators (2), or cyclic AMP analogues (3). Octopamine agonists (1) act by binding to a receptor which activates adenylate cyclase which, in turn, produces secondary messenger cyclic AMP. Enzyme stimulators (2) also act through the production of cyclic AMP, but do so by interacting directly with adenylate cyclase, bypassing the receptor. Once octopamine agonists or enzyme stimulators lead to the production of cyclic AMP, the cyclic AMP can bind to a cyclic AMP receptor generating hormonal-type activity. The third type of pest control compound, the cyclic AMP analogue (3), can bind to a cyclic AMP receptor generating hormonal-like activity.

Compounds (1), especially, are highly selective pest control agents since vertebrate species—as opposed to invertebrate, e.g., insect, species—lack octopamine receptors.

In another embodiment of the invention, there is provided a method for controlling pests by treating said pests with an agent as hereinabove in an amount effective to provide pest control, by either pesticidal or pestistatic activity.

DESCRIPTION OF THE PREFERRED EMBODIMENTS

Figure 1:
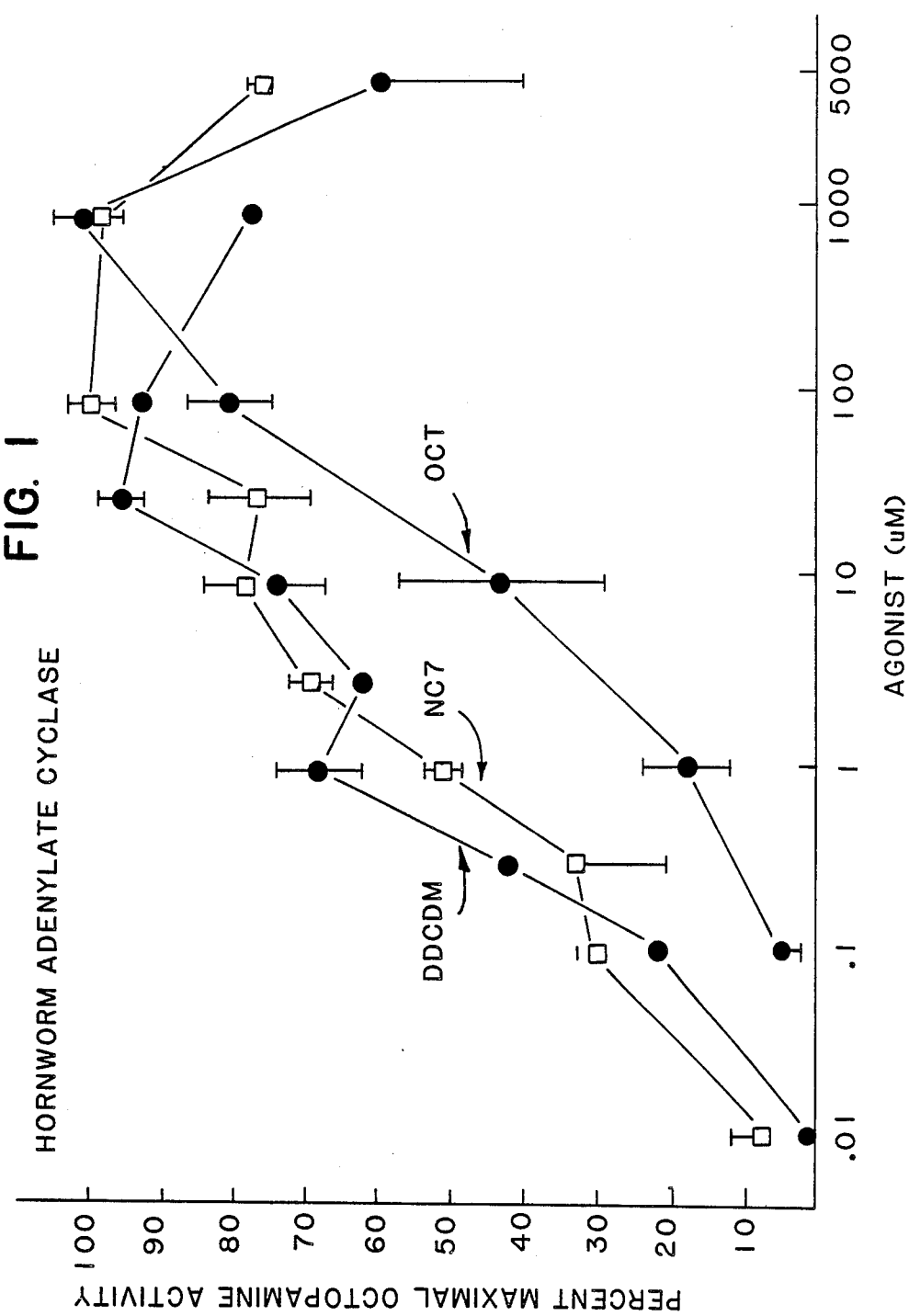
FIG. 1 shows that three compounds, octopamine, NC7 (a clonidine) and di-demethylchlordimeform (DDCDM), are potent activators of adenylate cyclase in the nerve cord of the tobacco hornworm.

The terms "pest controlling" or "pest controlling activity," used throughout the specification and claims, are meant to include any pesticidal (killing) or pestistatic (preventing the host plant from being eaten, or inhibiting, maiming or generally interfering) activities of a composition against a given pest at any stage in its life cycle. Thus, these terms not only include killing, but also include such activities as the production of behavioral abnormalities (e.g., tremor, incoordination, hyperactivity, anorexia, leaf walk-off behavior) which interfere with such activities such as but not limited to eating, molting, hatching, mobility or plant attachment. The terms also include activities of chemisterilants which produce sterility in insects by preventing the production of ova or sperm, by causing death of sperm or ova, or by producing severe injury to the genetic material of sperm or ova, so that the larvae that are produced do not develop into mature progeny.

The terms also include repellants, which are substances that protect animals, plants or products from insect attack by making food or living conditions unattractive or offensive. These may be poisonous, mildly toxic, or non-poisonous.

The terms also include attractants, food lures, sex pheromones, aggregation pheromones, and the like. Any compound which has such "pest controlling activity" as defined and which is (1) a non-formamidine octopamine agonist toward a an (−)-p-octopamine receptor present in the pest, (2) a direct stimulator of adenylate cyclase, or (3) a cyclic AMP analogue, is included in the present invention.

The question of whether a given compound (1) is a non-formamidine octopamine agonist can be readily answered by measuring adenylate cyclase activity of the octopamine-sensitive adenylate cyclase present in broken cell preparations of the firefly light organ. Generally, the broken cell preparations are prepared according to the method described in a paper by Nathanson et al. (*Molecular Pharmacology* 20: 68–75 (1981), which is herein incorporated by reference. Specimens of *Photinus pyralis* are prepared by opening their tail sections, cleaning them, removing the light organs, and homogenizing the cyclase-containing fraction. Adenylate cyclase activity is measured in appropriate buffer-containing ATP and the compound to be tested. If necessary, the compounds (1) to be tested are initially solubilized and appropriate solvent controls are run in parallel. The enzyme reaction is initiated by addition of ATP, stopped by heating, and centrifuged. Cyclic AMP can be measured by any test which indicates the presence thereof, preferably by the protein binding assay of Brown et al. (*Advances in Cyclic Nucleotide Research* 2: 25–40 (1972)). Normally, the solution mixture contains a phosphodiesterase inhibitor such as theophylline, so as to provide linear measurements with respect to time and enzyme concentration. The determination of the constant $K_a$, which is the concentration of agonist (1) necessary for half-maximal activation of cyclase activity, is carried out by measuring cyclase activity in the preparation, and plotting the activity (above control activity) versus the semilogarithm of the particular agonist concentration. This is done for a series of increasing concentrations until maximal activity (Vmax) is reached. $K_a^{(1)}$ is then calculated from the graph as the agonist concentration required for one-half of Vmax. $K_a^{(1)}$ is compared with the constant ($K_a^{oct}$) determined in an analogous way using ±p-octopamine as the agonist. The ratio $K_a^{oct}/K_a^{(1)}$ is then an indication of whether the compound (1) is better (ratio greater than 1) or worse (ratio smaller than 1) than (±)-p-octopamine. Maximal activation of enzyme activity as a percentage of maximal activation seen in the presence of (±) p-octopamine can be denoted as % Vmax. (Although the naturally occurring insect neurotransmitter is (−)-p-octopamine, the definition of an "agonist" in the present application is based on (±)-p-octopamine as the standard. Since an "agonist" is a compound that mimics the effect of (−)-p-octopamine, (−)p-octopamine itself, free of substantial amounts of the (+) enantioner is not included in the definition).

Generally, an octopamine agonist having a $K_a^{oct}/K_a^{(1)}$ ratio greater than 0.05, preferably 0.05 to 1000, most preferably 0.1 to 1000, as measured by the firefly lantern test, is used. Also, generally, octopamine agonists having Vmax anywhere between 5 and upwards of 100%, preferably between 10 and upwards of 100%, of the Vmax of (±)-p-octopamine can be used. The values of Vmax for any desired octopamine agonist are not as important as the values of the ratio of K's. As long as the $K_a^{oct}/K_a^{(1)}$ ratio falls within the stated range, the Vmax values can vary widely.

In addition to the above method employing the firefly light organ, octopamine-sensitive adenylate cyclase can also be measured in tissue preparations from the nerve cord of any desired particular insect pest, using a modification of the method appearing in Nathanson et al. (*Science* 180: 308–310 (1973)) herein incorporated by reference. In this modification (which is not necessary if the firefly light organ is used), dopamine (10 micromolar) and serotonin (10 micromolar) are added to all (including control) assay tubes. This is done in order to be sure that the tested compounds (1) are affecting only octopamine receptors (known to be present in all insect nerve cords) and not dopamine or serotonin receptors. Otherwise, the procedure is identical to that described above.

By "formamidines" are meant compounds of formula (I):

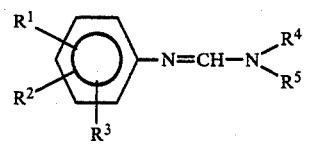

$R^4$ and $R^5$ stand for hydrogen, lower alkyl or lower alkyl substituted by hydroxy or lower ($C_1$-$C_6$) alkoxy. $R^1$, $R^2$, $R^3$ are the same or different and selected from the group consisting of hydrogen, hydroxy, fluorine, chlorine, bromine, iodine, nitro, lower ($C_1$-$C_6$) alkyl, lower ($C_1$-$C_6$) alkoxy, lower haloalkyl, amino, mono lower alkyl amino, di-lower alkyl amino, hydroxy-substituted lower alkyl and lower acylamino.

Among the preferred non-formamidine octopamine agonists (1) are those belonging to the families of the phenylethylamines (II):

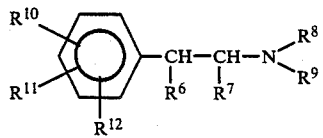

Cyclic Amidines (III):

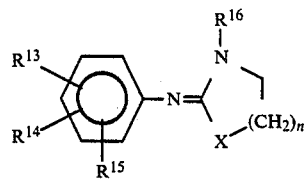

where X is N—$R^{16}$, O, $CH_2$, or S, and n may be 1 or 2; such as 2-(phenylimino) imidazolidines (X=NH, n=1); 2-(phenylimino) pyrrolidines (X=$CH_2$, n=1); 2-(phenylimino) oxazolidines (X=O, n=1); 2-(phenylimino) thiazolidines (X=S, n=1) and 2-(phenylimino) thiazines (X=S, n=2). See, e.g., the compounds in DeJong et al, Europ. J. Pharm. 69: 175-188 (1981);

2-benzylimidazolines (IV):

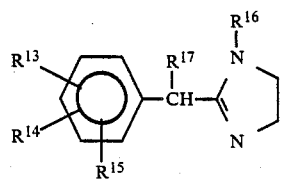

$R^8$, $R^9$, $R^{16}$ stand for hydrogen, lower alkyl or lower alkyl substituted by hydroxy or lower ($C_1$-$C_6$) alkoxy;

$R^{17}$ is hydrogen or hydroxy. $R^6$ and $R^7$ are the same or different and selected from the group consisting of hydrogen, hydroxy and lower ($C_1$-$C_6$) alkyl. $R^{10}$, $R^{11}$, $R^{12}$, $R^{13}$, $R^{14}$, $R^{15}$ are the same or different and selected from the group consisting of hydrogen, hydroxy, fluorine, chlorine, bromine, iodine, nitro, lower ($C_1$-$C_6$) alkyl, lower ($C_1$-$C_6$) alkoxy, lower haloalkyl, amino, mono lower alkylamino, di-lower alkyl amino, hydroxy substituted lower alkyl and lower acylamino.

Also, in compounds of formulae (III) or (IV) above, $R^{13}$, $R^{14}$ or $R^{13}$, $R^{15}$ together may form a six membered phenyl, pyridine, diazine, or cyclohexyl ring fused to the noted phenyl ring. For example, systems of formulae V and VI can also be used:

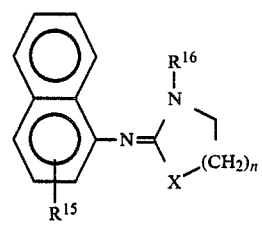

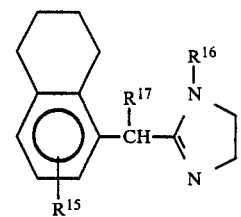

where $R^{15}$, $R^{16}$, $R^{17}$, and n are as defined previously.

Specific compounds useful as non-formamidine octopamine agonists (1) include phenylethylamines of the formula (VII):

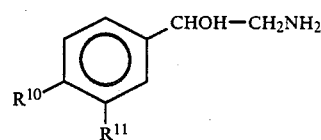

where $R^{10}$ is OH and $R^{11}$ is $CH_3$, $C_2H_5$, i—$C_3H_7$, $C_6H_{11}$, $NH_3$, F, Cl, Br I, $NHSO_2CH_3$, OH, H or $OCH_3$; or where $R^{11}$ is OH and $R^{10}$ i—$C_3H_7$, $CH_3$, $C_2H_5$, $C_6H_{11}$, $NH_3$, Cl, Br, I, NH—$SO_2CH_3$, $OCH_3$ or H.

Other specific compounds (1) include cyclic amidines of the formula (VIII):

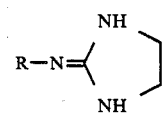

where R is phenyl; o-tolyl; 2,6 dimethylphenyl; 2,3(cyclohexyl) phenyl; 2,6-diethylphenyl; 2,6-difluorophenyl; 2-chlorophenyl; 2,6-dichlorophenyl; 3-chlorophenyl; 2,5-dichlorophenyl; 3,5-dichlorophenyl; 5-bromoquinoxaline; 2-methyl,3-bromophenyl; 2-chloro,4-methylphenyl; 3-fluoro,6-methylphenyl 2-chloro,3-methylphenyl; 2,6-dichloro, 4-hydroxphenyl; 3,4-dihydroxyphenyl; or 4-chlorophenyl.

Other specific compounds (1) include cyclic amidines of the formula (IX):

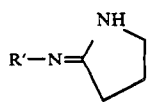

where R' is phenyl, o-tolyl, 2,6-dimethylphenyl, 2-chlorophenyl, 2,6-dichlorophenyl, 4-chlorophenyl, or 4-methoxyphenyl.

Other specific compounds (1) include cyclic amidines of the formula (X):

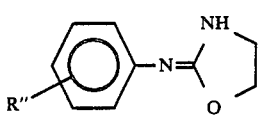

where R" is H, 2-CH$_3$, 2-6-diCH$_3$, 4-CH$_3$, 4-Cl or 2,6-diCl.

Other specific compounds (1) include cyclic amidines of the formula (XI):

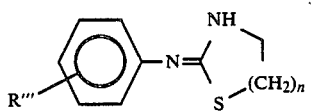

where R''' is 2,6-dimethyl; 2,6-dichloro; 2-6,diethyl; 2,4,6-trimethyl; 2,4-dichloro; 2,4-dimethyl; 2-chloro-4-methyl; 4-chloro-2-methyl; 4-chloro; 2-chloro; 2-methyl or 4-methyl; where n is 1 or 2.

Other specific compounds (1) include 2-benzylimidazoline of the formula (XII):

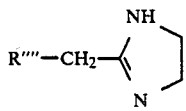

where R'''' is phenyl, o-tolyl, 2,6-dichlorophenyl, 4-CH$_3$O phenyl, 2,3 naphthyl (naphazoline), 2,6-dimethyl, 4-$^t$Butylphenyl (xylometazoline), 2,6-dimethyl, 3-hydroxy, 4-$^t$Butylphenyl (oxymetazoline), or or

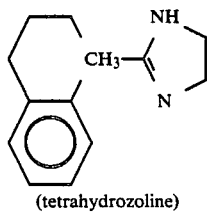

(tetrahydrozoline)

The syntheses and preparation of phenylethylamines of formula (II) is described, for example, in LeClerc et al., *J. Med. Chem.* 23: 738–744 (1980). The syntheses and preparation of cyclic amidines of formulas (III) or (IV) is described, for example, in Rouot, et al., *Journal of Medicinal Chemistry*, Vol. 19, 1049 (1976); Oxley et al, *J. Chem Soc.*, 497 (1947), Faust et al., *J. Org. Chem.* 26: 4044 (1961); Van der Stelt et al., *Arzneim. Forsch* 15: 1251 (1965) or Jen et al., *J. Med. Chem* 15: 727 (1972) and ibid, 18: 90 (1975).

Other examples of specific compounds (1) which are octopamine agonists are listed in the Tables in the accompanying examples.

The second type of pest controlling compounds (2) useable in the present compositions are direct stimulators of the pest enzyme adenylate cyclase. These compounds bypass the receptor, and interact with one or another of the associated catalytic or regulatory subunits of adenylate cyclase, thereby stimulating the formation of cyclic AMP. Suitable compounds can be determined from assay of pest adenylate cyclase as described above. Generally, a compound (at a concentration of less than 1 millimolar) causing a stimulation of adenylate cyclase of at least 10% that due to a Vmax concentration of ($\pm$)-p-octopamine is preferred. A direct stimulator of adenylate cyclase can be distinguished from an octopamine agonist in that the stimulatory activity of the former (but not the latter) at a concentration causing half-maximal activation of the enzyme, is not significantly reduced by the addition of known octopamine receptor antagonists, such as phentolamine or cyproheptadine, used at a concentration of 100 micromolar.

Among preferred direct enzyme stimulators are those belonging to the diterpenes, (XIII), forskolin (XIV) and its derivatives:

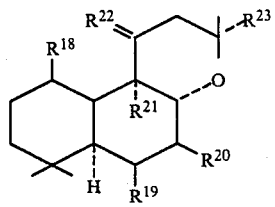

R$^{18-23}$ stand for hydrogen, hydroxyl, oxy, keto, lower alkyl, lower alkene, lower alkoxy, carboxy and carboxyamino.

In forskolin, R$^{18}$=R$^{19}$=R$^{21}$=OH; R$^{20}$=OCOMe; R$^{22}$=0; and R$^{23}$=CH=CH$_2$.

Certain bacterial-derived toxins, such as cholera toxin can also be used as enzyme stimulators.

The preparation of forskolin derivatives is described in Seamon, K. and Daly, J. W., *J. Med. Chem.* 26: 436–439 (1983). The structure and action of cholera toxin are described in Van Heyningen, S., *Biosci. Repts.* 2: 135–146 (1982).

The third type of pest controlling compounds (3) useable in the present invention are cyclic adenosine monophosphate analogues. These are compounds which have cyclic AMP activity, and are capable of binding to the appropriate pest protein kinase to activate the same. The potency of a particular cyclic AMP analogue can be determined from the calculated K$_a$ and Vmax of the analogue for activating cyclic AMP-dependent protein kinase found in insect nerve cord or firefly lantern, using the method described by Nathanson in *Cyclic AMP: A Possible Role in Insect Nervous System Function*, Ph.D. Thesis, Yale Univ., 1973, pp. 81–82, herein incorporated by reference. The K$_a$ and Vmax for the analogue can be compared, in the same tissue, with the K$_a$ and Vmax for cyclic AMP, itself, in stimulating protein kinase.

Generally, a cyclic AMP analogue with a K$_a$$^{(3)}$/K$_a$ (cyclic AMP) ratio greater than 0.01, preferably about 0.01 to 100 or more, most preferably 0.05 to 100 or more is used. Also, generally, cyclic AMP analogues having a Vmax anywhere between 5 and upwards of 100% of the Vmax for cyclic AMP can be used.

A number of biologically active cyclic AMP analogues have been synthesized. See Revankar and Robins, in *Handbook of Experimental Pharmacology*, 58/I (ed. J. Nathanson, J. Kebabian) pp. 17-151 (Spring-Verlag, N.Y.) 1982. Among the preferred ones are 6-n-butylamino-8-benzylthio-cyclic AMP; 8-p-chlorophenylthio-cyclic AMP; 8-chloro-cyclic AMP; 8-bromo-cyclic AMP; $N^6$-monobutyryl or $N^6,2'$-0-dibutyryl cyclic AMP; 7-deaza-cyclic AMP; and 1-deaza-cyclic AMP.

The molecular effects of compounds (1), (2) or (3) in vitro correlate with the molecular effects in vivo. However, it may be that a compound which is an excellent agonist, stimulator or analogue in vitro does not show good in vivo activity. Other factors, such as possible metabolism, transport or absorption of the compound may influence its overall effectiveness. One of skill in the art, however, can by a simple preliminary trial on the desired pest ascertain quite quickly and routinely whether a chosen agent is useful in vivo.

In a preferred embodiment the agents (1), (2) or (3) are used in combination with phosphodiesterase (PDE) inhibitors, to yield synergistic pest controlling compositions. The PDE inhibitors decrease a side reaction which causes hydrolysis and/or breakdown of the compound itself (in the case of cAMP analogues) or of secondary messenger cAMP (in the case of octopamine agonists or enzyme stimulators).

It should be noted that applicant has filed on May 1, 1984 commonly assigned patent application entitled "Pest Controlling Compositions" having Ser. No. 06/605,845, now abandoned which discloses compositions of octopamine agonists (1), enzyme stimulators (2), or cAMP analogues (3) with PDE inhibitors. The full disclosure of this copending patent application is herein incorporated by reference.

The pest controlling agents of the present invention can be formulated as dusts, water dispersions, emulsions, and solutions. They may comprise accessory agents such as dust carriers, solvents, emulsifiers, wetting and dispersing agents, stickers, deodorants and masking agents (see for example, *Encyclopedia of Chemical Technology*, Vol. 13, page 416 et seq.).

Dusts generally will contain low concentration, 0.1–20%, of the compounds, although ground preparations may be used and diluted. Carriers commonly include organic flours, sulfur, silicon oxides, lime, gypsum, talc, pyrophyllite, bentonites, kaolins, attapulgite, and volcanic ash. Selection of the carrier can be made on the basis of compatibility with the desired pest control composition (including pH, moisture content, and stability), particle size, abrasiveness, absorbability, density, wettability, and cost. The agent of the invention alone or in combination and diluent is made by a variety of simple operations such as milling, solvent impregnations, fusing and grinding. Particle sizes usually range from 0.5–4.0 microns in diameter.

Wettable powders can be prepared by blending the agents of the invention in high concentrations, usually from 15–95%, with a dust carrier such as bentonite which wets and suspends properly in water. 1 to 2% of a surface-active agent is usually added to improve the wetting and suspendibility of the powder.

The pest-controlling agents can also be used in granules, which are pelleted mixtures of the agents, usually at 2.5–10%, and a dust carrier, e.g., adsorptive clay, bentonite or diatomaceous earth, and commonly within particle sizes of 250 to 590 microns. Granules can be prepared by impregnations of the carrier with a solution or slurry of the agents and can be used principally for mosquito larvae treatment or soil applications.

The agents can also be applied in the form of an emulsion, which comprises a solution of the agents in water immiscible organic solvents, commonly at 15–50%, with a few percent of surface active agent to promote emulsification, wetting, and spreading. The choice of solvent is predicated upon solubility, safety to plants and animals, volatility, flammability, compatibility, odor and cost. The most commonly used solvents are kerosene, xylenes, and related petroleum factions, methylisobutylketone and amyl acetate. Water emulsion sprays from such emulsive concentrates can be used for plant protection and for household insect control.

The agents can also be mixed with baits, usually comprising 1–5% of agents with a carrier especially attractive to insects. Carriers include sugar for house flies, protein hydrolysate for fruit flies, bran for grasshoppers, and honey, chocolate or peanut butter for ants.

The agents can be included in slow release formulations which incorporate non-persistent compounds, insect growth regulators and sex pheromones in a variety of granular microencapsulated and hollow fiber preparations.

The pest controlling agents of the present invention will be applied depending on the properties of the particular pest controlling compound, the habits of the pest to be controlled and the site of the application to be made. It can be applied by spraying, dusting or fumigation.

Doses of the weight of the ingredients may typically vary between 0.001–100 lbs/acre, preferably between 0.001–5 lbs/acre.

Sprays are the most common means of application and generally will involve the use of water as the principal carrier, although volatile oils can also be used. The pest-control agents of the invention can be used in dilute sprays (e.g., 0.001–10%) or in concentrate sprays in which the composition is contained at 10–98%, and the amount of carrier to be applied is quite reduced. The use of concentrate and ultra low volume sprays will allow the use of atomizing nozzles producing droplets of 30 to 80 microns in diameter. Spraying can be carried out by airplane or helicopter.

Aerosols can also be used to apply the pest controlling agents. These are particularly preferred as space sprays for application to enclosures, particularly against flying insects. Aerosols are applied by atomizing amounts of liquified gas dispersion or bomb but can be generated on a larger scale by rotary atomizers or twin fluid atomizers.

A simple means of pest control agent dispersal is by dusting. The pest controlling agent is applied by introducing a finely divided carrier with particles typically of 0.5–3 microns in diameter into a moving air stream.

Any octopamine-receptor containing pest is treatable by the formulation of the present invention. These pests include all invertebrate pests, including, but not limited to, round worms (e.g., hookworm, trichina, ascaris); flatworms (e.g., liver flukes and tapeworms); jointed worms (e.g., leeches); molluscs (e.g., parasitic snails); and arthropods (insects, spiders, centipedes, millipedes, crustaceans (e.g., barnacles)). In particular, included among the arthropods are ticks; mites (both plant and animal); lepidoptera (butterflies and moths and their larvae); hemiptera (bugs); homoptera (aphids, scales); and coleoptera (beetles). Also included are spiders; anoplura (lice); diptera (flies and mosquitoes); trichoptera; orthoptera (e.g., roaches); odonta; thysanura (e.g., silverfish); collembola (e.g., fleas); dermaptera (earwigs); isoptera (termites); ephemerids (mayflies)); plecoptera; mallophaga (biting lice); thysanoptera; and siphonaptera (fleas); dictyoptera (roaches); psocoptera (e.g., booklice); and certain hymenoptera (e.g., those whose larva feed on leaves).

EXAMPLES

Having now generally described this invention, the same will become better understood by reference to certain specific examples which are included herein for purposes of illustration only and are not intended to be limiting unless otherwise specified.

IN VITRO METHODS

I. Determination of Octopamine Agonist Activity

A. Firefly Light Organ

Specimens of *Photinus pyralis* were collected in summer, frozen on dry ice, and stored at −90°. Under these conditions, octopamine sensitive enzyme activity remains stable for six months or longer. For each experiment, a number of insects were thawed and maintained at 4° C. Tail sections were opened through a dorsal midline incision and the abdominal cavity was cleaned out of all gut, fat reproductive organs, and ganglia. The light organs were then removed from the ventral cuticle, cleaned of any adhering nonlantern tissue, and homogenized (10 mg/ml) in 6 mM Tris-maleate buffer (pH 7.4). To prepare a $P_2$ fraction, the homogenate was diluted to a volume of 30 ml in 6 mM Tris-maleate and centrifuged at $120,000 \times g$ for 20 minutes. The supernatant was discarded, and the pellet was resuspended by homogenization in 30 ml of buffer and again centrifuged at $120,000 \times g$ for 20 minutes. The resulting pellet ($P_2$ fraction) was resuspended in a volume of 6 mM Tris-maleate equivalent to the starting amount and maintained at 0° until it was used. Alternatively, the homogenate may be used directly without preparing $P_2$ fraction.

Adenylate cyclase activation by test compounds was measured in test tubes containing (in 0.3 ml) 80 mM Tris-maleate, pH 7.4; 10 mM theophylline; 8 mM $MgCl_2$; 0.1 mM GTP; 0.5 mM ethylene glycol bis (beta-aminoethyl ether)-N,N,N'N'-tetraacetic acid; 2 mM ATP; 0.06 ml of $P_2$ fraction; and the various compounds to be tested. Prior experiments had determined that, under these conditions, octopamine-sensitive adenylate cyclase activity is optimized. Test compounds were initially solubilized (prior to aqueous dilution) in water or (if soluble) in 50% (v/v) methanol. If insoluble in 50% methanol, compounds may be dissolved initially in 100% methanol, or 100% dimethylsulfoxide, or 100% polyethylene glycol. Final solvent concentration after dilution can be kept as high as 15% for methanol and DMSO and as high as 20% for polyethylene glycol. Appropriate solvent controls were run in parallel. The enzyme reaction (5 minutes at 30°) was initiated by addition of ATP, stopped by heating to 90° for 2 minutes, and then centrifuged at $1000 \times g$ for 15 minutes to remove insoluble material. Cyclic AMP in the supernatant was measured by protein-binding assay, according to the method of Brown et al., *Adv. Cyclic Nucleotide Res.* 2: 25–40 (1970). Under the above assay conditions, enzyme activity is linear with respect to time and enzyme concentration, and phosphodiesterase activity is nearly completely inhibited. Previous experiments had shown that the cyclic AMP produced in this reaction cochromatographs on Dowex AG-50X[R] resin with authentic cyclic AMP. Protein concentration was determined by the method of Lowry et al., *Journal of Biological Chemistry* 193: 265–275 (1951).

B. Other Pest Tissues

In those cases in which other pest tissues are used to measure octopamine agonist activity, the procedure is identical to that above, except that the tissue to be used is the brain, segmental ganglia, or the entire nerve cord of the insect pest, with or without the brain. The tissue is homogenized (usually 15 mg/ml) as above in 6 mM Tris maleate, pH 7.4. Assay conditions are identical to those described above except that dopamine (10 micromolar) and serotonin (10 micromolar) are added to all (including control) assay tubes when testing compounds which may affect receptors other than octopamine receptors. This is done to cancel out the effects of dopamine and serotonin receptors which are usually present in nerve cord. It assures that the compound tested is affecting only octopamine receptors (known to be present in all insect nerve cords).

II. Determination of Adenylate Cyclase Stimulating Activity

As detailed previously, the adenylate cyclase assay, either in the firefly or in other insect pest, is also used to identify a direct stimulator of adenylate cyclase.

III. Determination of Cyclic AMP-Dependent Protein Kinase Activity (for Determination of Activity of Cyclic AMP Analogues)

A $P_2$ pellet is prepared as described above from either firefly lantern or insect pest nerve tissue. In this assay, the pellet is used both as a source of protein kinase and as the substrate which is phosphorylated. The assay mixture (total volume 0.2 ml) contains: 10 micromoles sodium glycerol phosphate buffer, pH 7.4; 1 millimicromole gamma-$^{32}$P-ATP, approx. $10^6$ cpm; 2 micromoles $MgCl_2$; 2 micromoles NaF; 0.4 micromoles theophylline; 0.06 micromoles EGTA; 10–100 micrograms protein of $P_2$ pellet; ± various concentrations of cyclic AMP or the cyclic AMP analogue to be tested (typically to give a final concentration of from $10^{-9}$–$10^{-4}$M).

The reaction is initiated by the addition of tissue and the incubation is for 5 minutes at 30° C. The reaction is terminated by the addition of 4 ml of 7.5% trichloroacetic acid (TCA). 0.2 ml of 0.63% bovine serum albumin is added, the mixture is centrifuged at low speed, and the supernatant is discarded. The precipitate is dissolved in 0.1 ml of 1N NaOH and the TCA precipitation repeated 4 more times. The protein-bound $^{32}$P is then dissolved in NaOH and counted in a scintillation spectrometer. The amount of increase in cpm over control tubes incubated in the absence of cyclic AMP or cyclic AMP analogue represents cyclic-AMP-dependent protein kinase activity. Activity constants are calculated as described previously.

IN VIVO METHODS

To test the pesticidal and pestistatic effects of some of the disclosed compounds, the effects on the feeding behavior of tobacco hornworms (*Manducca sexta*) were investigated. This species is one of the several types of insects particularly susceptible to octopamine type insecticides. The ease of rearing this species from eggs in the laboratory and the ability to maintain them on artificial media, makes it possible to test compounds on large numbers of larvae of the same age.

For testing, single tomato leaves were placed in a closed container, with stems hydrated by means of a small, 3 ml water-filled bottle. Compounds, dissolved in water or methanol, were sprayed on the tomato leaves with an ultra fine atomizer. Six, 3-day-old larvae were placed on each leaf, allowed to feed for 24–108 hours, and then the percentage of leaf remaining was determined by planimetry, weight, or "blind" visual observation. An active compound was one which resulted in an increase in percentage of leaf remaining, compared with control.

In some cases, test agents were tested for ovacidal activity by dipping groups of 10–50 Manducca eggs in drug solutions for 60 seconds and then determining the percentage of eggs which produced viable larvae. A compound with active ovacidal activity was one which decreased the percentage of eggs hatched, relative to control.

EXAMPLE 1

Phenylethylamines as Octopamine Agonists

Table 1 shows the structure/activity relationships of phenylethylamines interacting with octopamine sensitive adenylate cyclase of the firefly (*Photinus pyralis*).

TABLE 1

Structure-activity Relationships of Phenylethylamines Interacting with Octopamine-sensitive Adenylate Cyclase

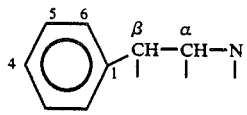

| Compound | | $\beta$ | $\alpha$ | N | Vmax (% OCT) | $\dfrac{K_a OCT}{K_a drug}$ |
|---|---|---|---|---|---|---|
| $\beta$-phenylethylamine | — | H | H | $H_2$ | 13 ± 2 | 0.03 |
| (+)-amphetamine | — | H | $CH_3$ | $H_2$ | N.A. | — |
| (±)-phenylethanolamine (-hydroxyphenyl ethylamine) | — | OH | H | $H_2$ | 45 ± 1 | 0.11 |
| (±)-norephedrine (phenylpropanolamine) | — | OH | $CH_3$ | $H_2$ | 8 ± 1 | <0.09 |
| (±)-o-octopamine | 2-OH | OH | H | $H_2$ | 23 ± 1 | 0.05 |
| (±)-m-octopamine (norphenylephrine) | 3-OH | OH | H | $H_2$ | 9 ± 1 | 0.1 |
| (−)-phenylephrine | 3-OH | OH | H | $HCH_3$ | 17 ± 1 | <0.2 |
| tyramine | 4-OH | H | H | $H_2$ | 57 ± 1 | 0.15 |
| (±)-p-hydroxyamphetamine | 4-OH | H | $CH_3$ | $H_2$ | 8 ± 3 | <0.05 |
| (±)-p-octopamine | 4-OH | OH | H | $H_2$ | 81 ± 1 | 0.06 |
| (±)-p-octopamine | 4-OH | OH | H | $H_2$ | 100 ± 1 | 1.0 |
| (−)-p-octopamine (natural) | 4-OH | OH | H | $H_2$ | 101 ± 2 | 1.3 |
| (±)-N—methyloctopamine (synephrine) | 4-OH | OH | H | $HCH_3$ | 108 ± 10 | 1.8 |
| (±)-$\alpha$-methyloctopamine (p-hydroxynorephedrine) | 4-OH | OH | $CH_3$ | $H_2$ | 44 ± 2 | 0.05 |
| (±)-N,N—dimethyl-octopamine | 4-OH | OH | H | $(CH_3)_2$ | 43 ± 4 | 0.9 |
| (±)-$\alpha$-methylsynephrine (p-hydroxyephedrine) | 4-OH | OH | $CH_3$ | $HCH_3$ | 7 ± 2 | <0.01 |
| p-hydroxymandelic acid | 4-OH | OH | OHO | — | N.A.* | — |
| isoxsuprine | 4-OH | OH | $CH_3$ | 1** | N.A. | — |
| p-methoxyphenylethylamine (p-methoxytyramine) | 4-$OCH_3$ | H | H | $H_2$ | 6 ± 3 | 0.10 |
| p-fluoro-phenylethanolamine | 4-F | OH | $H_2$ | $H_2$ | 72 ± 8 | 0.11 |
| 2,4-dichlorophenylethanolamine | 2-Cl, 4-Cl | OH | H | $H_2$ | 14 ± 1 | 0.67 |
| m-chloro-octopamine | 3-Cl, 4-OH | OH | H | $H_2$ | 77 ± 1 | 0.28 |
| dopamine | 3-OH, 4-OH | H | H | $H_2$ | 4 ± 1 | 0.26 |
| N—methyldopamine | 3-OH, 4-OH | H | H | $HCH_3$ | 11 ± 1 | 0.19 |
| (−)-nonrepinephrine | 3-OH, 4-OH | OH | H | $H_2$ | 72 ± 1 | 0.13 |
| (−)-epinephrine | 3-OH, 4-OH | OH | H | $HCH_3$ | 75 ± 2 | 0.20 |
| (−)-isoproterenol | 3-OH, 4-OH | OH | H | $HCH(CH_3)_2$ | 19 ± 1 | <0.03 |
| (±)-normetanephrine | 3-$OCH_3$, 4-OH | OH | H | $H_2$ | 68 ± 2 | 0.07 |
| salbutamol | 3-$CH_2$—OH, 4-OH | OH | H | $HC(CH_3)_3$ | N.A. | — |

TABLE 1-continued

Structure-activity Relationships of Phenylethylamines
Interacting with Octopamine-sensitive Adenylate Cyclase

[Structure: phenyl ring with positions 3,4,5,6 labeled, with side chain $\beta$CH—$\alpha$CH—N]

| Compound | | | | Vmax (% OCT) | $\frac{K_aOCT}{K_a drug}$ |
|---|---|---|---|---|---|
| zinterol | 3-NHSO$_2$CH$_3$, 4-OH | OH | H | 2** | N.A. | — |

[a] No Activity

[**1] CH—CH$_2$O—[phenyl]
     |
     CH$_3$

[**2] —C(CH$_3$)$_2$—CH$_2$—CH$_2$—[phenyl]

i.e., —C(=O)—OH

It can be seen that in most instances the half-maximal activation constant $K_a$ for the desired pest controlling compound ranges between less than 0.01 of (±)-p-octopamine to greater than (±)-p-octopamine, whereas the Vmax ranges from less than 4 to 108% of Vmax of octopamine. Examples of compounds satisfying the criteria of most preferred octopamine agonists ($K_a^{oct}/K_a^B > 0.1$; Vmax > 10%) are p-octopamine, N-methyl-octopamine, p-fluoro-phenylethanolamine, and 2,4-dichlorophenylethanolamine. Note here that m-octopamine has much less activity than the active positional isomer, p-octopamine. As will be shown below, and confirming the in vitro/in vivo correlation m-octopamine also has much less pesticidal activity than p-octopamine, and the activity shows much less synergism.

EXAMPLE 2

Clonidines as Octopamine Agonists

A number of clonidine analogues were investigated as octopamine agonists in the octopamine receptor of the firefly lantern. Inhibitory properties were also tested. Table 2 shows the results of these experiments.

TABLE 2

OCTOPAMINE RECEPTOR ACTIVITY OF THE CLONIDINES

[Structure: phenyl ring with positions 2,3,4,5,6, substituted at position 1 with —N=C(NH)(NH) imidazolidine ring]

| Compound | Substituents | Vmax (% OCT) | $\frac{K_aOCT}{K_a drug}$ | $K_i$ (μm) |
|---|---|---|---|---|
| NC 10 | — | N.A. | N.A. | 190 |
| NC 12 | 4-Br | 34 | 3.0 | — |
| NC 8 | 2-Cl, 4-Cl | 47 | 3.7 | — |
| NC 7 | 2-CH$_3$, 4-Cl | 68 | 9.8 | — |
| NC 9 | 2-CH$_3$, 4-CH$_3$ | 78 | 5.1 | — |
| NC 2 | 2-Cl, 5-Cl | 9 | 1.1 | 23 |
| NC 6 | 2-Br, 6-Br | 35 | 2.1 | — |
| clonidine | 2-Cl, 6-Cl | 35 | 0.95 | 20 |
| NC 4 | 2-CH$_3$, 6-CH$_3$ | 80 | 0.41 | — |
| NC 5 | 2-CH$_2$CH$_3$, 6-CH$_2$CH$_3$ | 97 | 19.0 | — |
| NC 3 | 2-Cl, 4-Cl, 5-Cl | 80 | 2.8 | — |
| NC 11 | 2-Cl, 4-Cl, 6-Cl | 60 | 1.9 | — |
| NC 13 | 2-CH$_3$, 4-CH$_3$, 6-CH$_3$ | 112 | 4.3 | — |
| NC 14 | 2-Cl, 4NH$_2$, 6-Cl | 29 | 0.7 | 440 |
| NC 15 | 2-Cl, 4-N(CH$_3$)$_2$, 6-Cl | 38 | 1.9 | — |

TABLE 2-continued

OCTOPAMINE RECEPTOR ACTIVITY OF THE CLONIDINES

| Compound | Substituents | Vmax (% OCT) | $\frac{K_aOCT}{K_a drug}$ | $K_i$ (μm) |
|---|---|---|---|---|
| NC 16 | 2-Cl, 4-NCH$_3$(CH$_2$CH$_2$Cl), 6-Cl | 6 | 4.8 | 10 |
| NC 17 | 2-Cl, 4-CH$_2$NCH$_3$(CH$_2$CH$_2$Cl), 6-Cl | N.A. | N.A. | 250 |

Among the findings resulting from this data was the fact that several clonidine derivatives (some having low mammalian potency) are extremely potent octopamine agonists. For example, 2-(2,6-diethylphenylimino) imidazolidine (NC5) was an extremely potent activator of light organ adenylate cyclase. Significant stimulation occurred at concentrations as low as $3 \times 10^{-8}$. The $K_a$ was about 1 μm (20-fold lower than that due to octopamine), and maximal stimulation was equal to that caused by octopamine. In experiments employing combinations of octopamine and NC5, it was found that stimulation by NC5 was non-additive with that due to octopamine, and that NC5 had no activity as an octopamine antagonist. It was also found that stimulation of enzyme activity by NC5 was reversible and could be inhibited by low concentrations of certain antagonists, such as cyproheptadine, which are known to inhibit stimulation by octopamine.

Similar to octopamine, NC5 showed a high degree of selectivity for tissues known to contain an octopamine-activated adenylate cyclase as compared with those containing dopamine- or adrenergic-stimulated adenylate cyclases. Thus, isoproterenol potently stimulates Beta$_1$ and Beta$_2$-adrenergic-stimulated adenylate cyclase in rat heart and liver. In the heart, octopamine caused only a small stimulation (16% that of isoproterenol) while NC5 was almost completely inactive. In the liver, neither octopamine nor NC5 were active. Similarly, in the rat caudate nucleus, although dopamine stimulated the dopamine-sensitive adenylate cyclase known to be present, neither octopamine nor NC5 caused any significant enzyme stimulation. In none of the three mammalian tissues did NC5 cause any inhibition of basal adenylate cyclase activity. Furthermore, other data indicated that the effects of the phenyliminoimidazolidines on octopamine-sensitive adenylate cyclase could be clearly distinguished from their effects on alpha-adrenergic receptors.

Other potent derivatives included: 2-methyl, 4-chloro (NC7) (potency ratio=9.8); 2,4-dimethyl (ratio=5.1); 2,4,6-trimethyl (ratio=4.3); 2,4-dichloro (ratio=3.7); and 2,4,5-trichloro (ratio=3.0). In prior physiological studies, it had been reported that clonidine, a 2,6-dichloro phenyliminoimidazolidine derivative, can stimulate octopamine receptors which may be distinct from those associated with adenylate cyclase (Evans, P. D., *J. Physiol.* 318: 99–122 (1981)). In the present studies, clonidine was much less potent than the above compounds (octopamine potency ratio=0.9). In addition, it was less effective ($V_{max}=35\%$ that of octopamine), and was a partial antagonist of octopamine-stimulated enzyme activity ($K_i=20$ μM).

To confirm that activation of octopamine-sensitive adenylate cyclase by the highly active phenyliminoimidazolidines was indicative of in vivo octopaminergic potency, some of the compounds were evaluated for their ability to stimulate light production when injected into the transected, isolated tails of Photinus males. The dose-response curves showed that, for a group of animals, octopamine stimulated light emission with an $EC_{50}$ for octopamine of about 5 nmoles/tail. NC5, in contrast, had an $EC_{50}$ of about 0.3 nmoles, and thus was more than 16 times as potent as octopamine. Relative to octopamine, NC5 was even more potent at low levels of stimulated light emission. At high doses, maximal stimulation by the two compounds was comparable and, at maximally effective doses, a combination of both compounds did not elicit more light production than either compound alone.

In order to confirm that the phenylimino-imidazolidines have anti-feeding behavioral actions, the effects of certain of these compounds, as well as octopamine, itself, were examined on the feeding behavior of *Manduca sexta* (tobacco hornworm) larvae. Application of octopamine to leaves resulted in a dose-dependent inhibition ($K_i$ 0.5 mg/leaf) of feeding by the larvae. 2-(2-methyl,-4-chlorophenylimino) imidazolidine (NC7) caused qualitatively similar effects but was over 15-fold more potent than octopamine ($K_i$ 0.01 mg/leaf). Larvae feeding on leaves treated with both compounds showed tremors, hyperactivity, and leaf walk-off behavior. At higher doses, larvae demonstrated particular difficulty during molting (a task demanding of motor coordination), frequently being unable to shed their old cuticle, and subsequently dying. Together, the in vivo studies confirm the in vitro screen, indicating that in vitro selected phenylimino-imidazolidines are very potent agonists of octopamine-sensitive cyclase.

EXAMPLE 3

Demonstration of Octopamine Agonist Activity Measured in Tissue from an Insect Pest In order to show that adenylate cyclase activation in tissue from an insect pest can also be used to define octopamine agonists, members of three chemical groups (phenylethanolamines, phenyliminoimidazolidines, and formamidines) were tested for their ability to activate adenylate cyclase in broken cell preparations of insect nerve cord. FIG. 1 shows that octopamine, NC7 (see Table 2), and DDCDM were potent activators of adenylate cyclase in nerve cord of tobacco hornworm. Octopamine and NC7 fulfilled the criteria of being most preferred octopamine agonists. As will be described below, these compounds have pesticidal activity.

EXAMPLE 4

Figure 2:
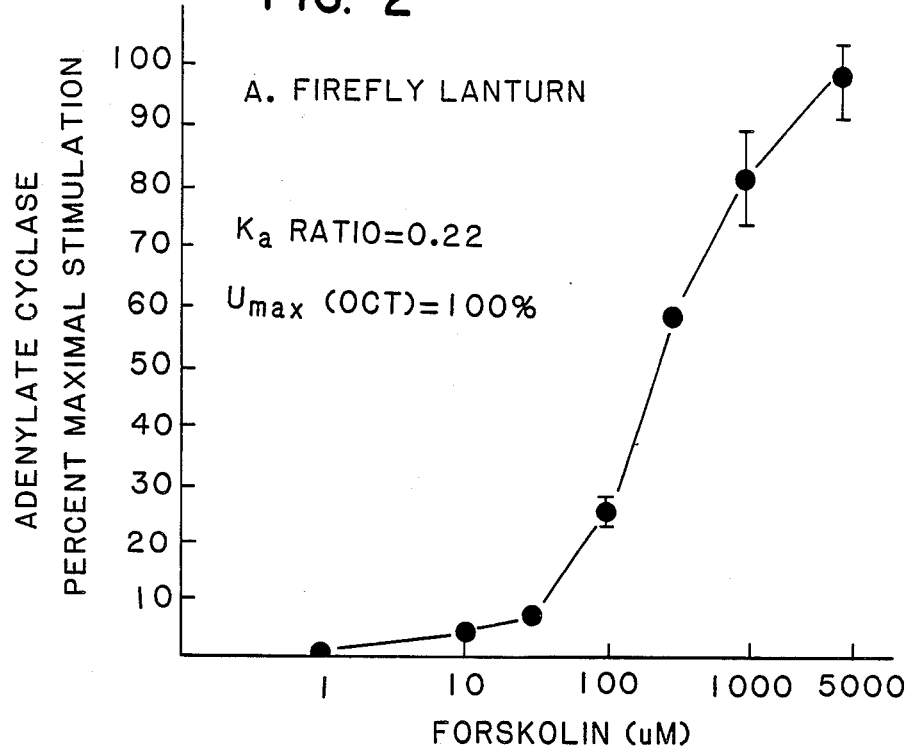
FIG. 2 shows the effect of forskolin in activating adenylate cyclase in the firefly lantern. $K_a$ ratio=0.22; $V_{max}$=100%.
Figure 3:
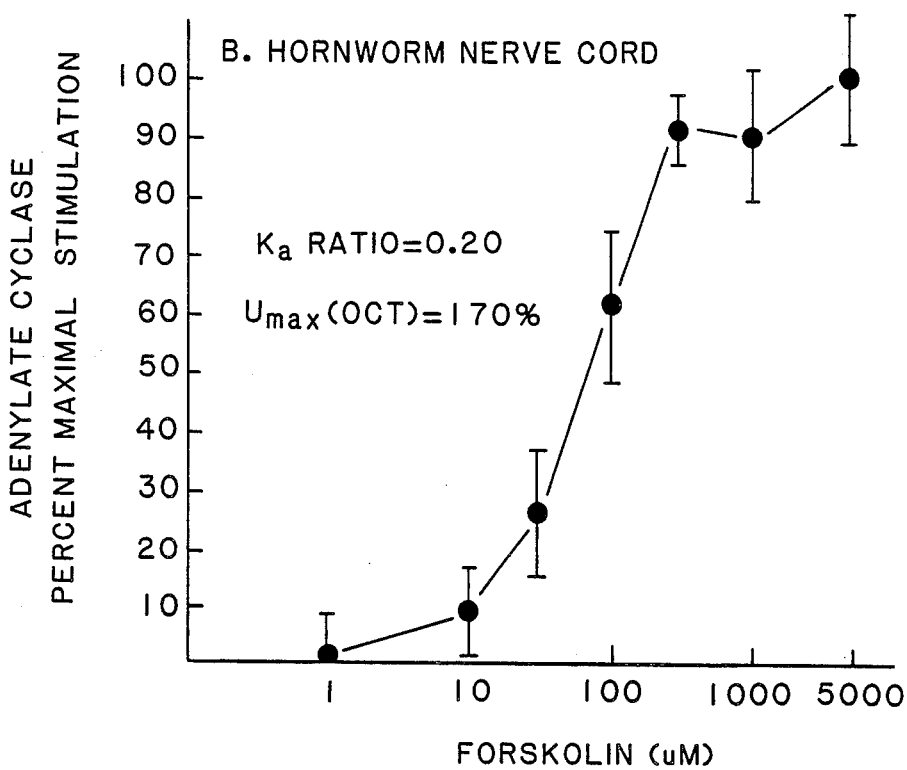
FIG. 3 shows the effect of forskolin in activating adenylate cyclase activity in broken cell preparations from the nerve cord of tobacco hornworm larvae. $K_a$ ratio=0.20; $V_{max}$=about 100%.

A Direct Stimulator of Adenylate Cyclase in the Firefly Lantern and in Pest Tissue FIG. 2 shows the effect of forskolin in directly activating adenylate cyclase in firefly lantern. FIG. 3 also shows the effect of forskolin in directly activating adenylate cyclase activity in broken cell preparations from the nerve cord of tobacco hornworm larvae. In both tissues, forskolin fulfills the criteria of a preferred enzyme activator. As will be shown below, forskolin has activity as a pesticide and this activity is synergized by phosphodiesterase inhibition.

EXAMPLE 5

Demonstration of Increased Cyclic AMP Content in Pest Nerve Cord Caused by a Combination of an Octopamine Agonist and a Phosphodiesterase Inhibitor As described earlier and as shown in Scheme I, the pesticidal activity of octopamine agonists is mediated through the increased formation of cyclic AMP within the cells of the insect pest. In order to directly demonstrate that a PDE inhibitor, as defined above, can augment the increase in cyclic AMP caused by an octopamine agonist (as defined above) in an insect pest, further experiments were run using intact nerve cords of tobacco hornworms. These intact nerve cords were incubated under physiological conditions in the presence of octopamine, NC7, or DDCDM, first in the absence of PDE inhibitor IBMX and then in the presence of 0.1 mM IBMX. After 5 minutes, the intact nerve cord was quickly treated to release all cyclic AMP which was present within the tissue.

Table 3 compares the levels of cyclic AMP within nerve tissue under different treatments. As can be seen, with all three octopamine agonists (octopamine, NC7, and DDCDM), addition of IBMX markedly increased the level of cyclic AMP within the nerve tissue.

TABLE 3

Effect of Octopamine Agonists and IBMX on Increasing Cyclic AMP in Insect Pest Tissue

| Compound | Cyclic AMP Content (Fold-increase over Control) | |
| --- | --- | --- |
| | −IBMX | +0.1 mM IBMX |
| Octopamine | 0.9 ± 0.3 | 6.4 ± 1.0 |
| NC 7 | 2.2 ± 0.2 | 13.9 ± 3.0 |
| DDCDM | 5.4 ± 3.8 | 11.1 ± 2.7 |

Also of considerable interest was the fact that, consistent with the invention, the level of cyclic AMP within the tissue paralleled pesticidal activity. Thus, in other experiments, it was determined that the rank order antifeeding effectiveness of the various compositions (based on the $EC_{50}$ of the octopamine agonist) shown was: DDCDM+IBMX=NC7+IBMX>Octopamine+IBMX=DDCDM alone>NC7 alone>octopamine alone. This order was identical to the rank order of the cyclic AMP levels shown in Table 3. Also note, for example, that, in the absence of IBMX, octopamine caused little elevation of cyclic AMP, and likewise had little pesticidal activity (see FIGS. 9, 10 below). In the presence of IBMX, however, octopamine considerably elevated both cyclic AMP content and pesticidal activity.

EXAMPLE 6

In Vivo Leaf Test of Compositions Containing Phenylethanolamines

Table 4 shows the results obtained for mixtures comprising various phenylethanolamines in the presence or absence of IBMX as a PDE inhibitor.

TABLE 4

| Agonist (gm/100 ml) | | % Leaf Remaining | |
|---|---|---|---|
| | | No PDE Inhibitor | PDE Inhibitor (0.1 g/100 ml) |
| 4-F-phenylethanol-amine | C* | <5 | IBMX 25 |
| | $10^{-3}$ | <5 | 50 |
| | $10^{-2}$ | <5 | 80 |
| | $10^{-1}$ | <5 | 98 |
| | 0.3 | 25 | 95 |
| 2,4-dichlorophenyl-ethanolamine | C* | <5 | IBMX 20 |
| | $10^{-2}$ | <5 | 30 |
| | $10^{-1}$ | <5 | 50 |
| | 1 | 10 | 80 |
| Synephrine | C* | <5 | IBMX 42 |
| | $10^{-2}$ | <5 | 42 |
| | $10^{-1}$ | <5 | 55 |
| | 1 | 30 | 90 |

*Control = No Agonist

The results show that the phenylethanolamines themselves had antifeeding activity and that, in all instances, addition of IBMX markedly enhanced the ability of the phenylethanolamines to inhibit the leaf feeding activity of the pest.

EXAMPLE 7

In Vivo Leaf Tests of Compositions Containing Phenyliminoimidazolidines (Clonidines).

Mixtures of various clonidine derivatives with or without IBMX were prepared and tested in the aforementioned in vivo tests. Table 5 shows the results.

TABLE 5

| Agonist (gm/100 ml) | | % Leaf Remaining | |
|---|---|---|---|
| | | No PDE Inhibitor | PDE Inhibitor (0.1 g/100 ml) |
| NC 7[1] | C* | 25 | IBMX 30 |
| | $10^{-3}$ | 23 | 48 |
| | $10^{-2}$ | 30 | 85 |
| | $10^{-1}$ | 55 | 95 |
| | $3 \times 10^{-1}$ | 80 | 100 |
| clonidine | C* | 5 | IBMX 35 |
| | $10^{-2}$ | 5 | 55 |
| | $10^{-1}$ | 20 | 55 |
| | 1 | 65 | 63 |
| NC 5[1] | C* | 10 | IBMX 18 |
| | $10^{-3}$ | 10 | 17 |
| | $10^{-2}$ | 15 | 30 |
| | $10^{-1}$ | 30 | 45 |
| | $3 \times 10^{-1}$ | 40 | 70 |
| NC 10[1] | C* | 10 | IBMX 15 |
| | $10^{-3}$ | 5 | 12 |
| | $10^{-2}$ | 5 | 15 |
| | $10^{-1}$ | 5 | 13 |
| | 1 | 5 | 15 |

[1]See Table 2, supra
*Control = No agonist

The data indicate that, with NC7, clonidine, and NC5, addition of IBMX results in substantial increases in the potency of the pest controlling compound. It will be noted that these three pest controlling compounds, on the basis of in vitro testing (Table 2), all satisfied the criteria of being most preferred compounds of type 1. Of interest, and further confirming the invention, was the fact that the structural analogue, NC10, was inactive in vivo. Thus, as can be seen in Table 5, NC10 lacked antifeeding activity both in the absence or presence of the PDE inhibitor, IBMX. This unexpected result was correctly predicted by the in vitro assay data shown in Table 2, where NC10 had no activity.

EXAMPLE 8

In Vivo Leaf Test of a Composition Containing a Direct Enzyme Stimulator

Figure 4:
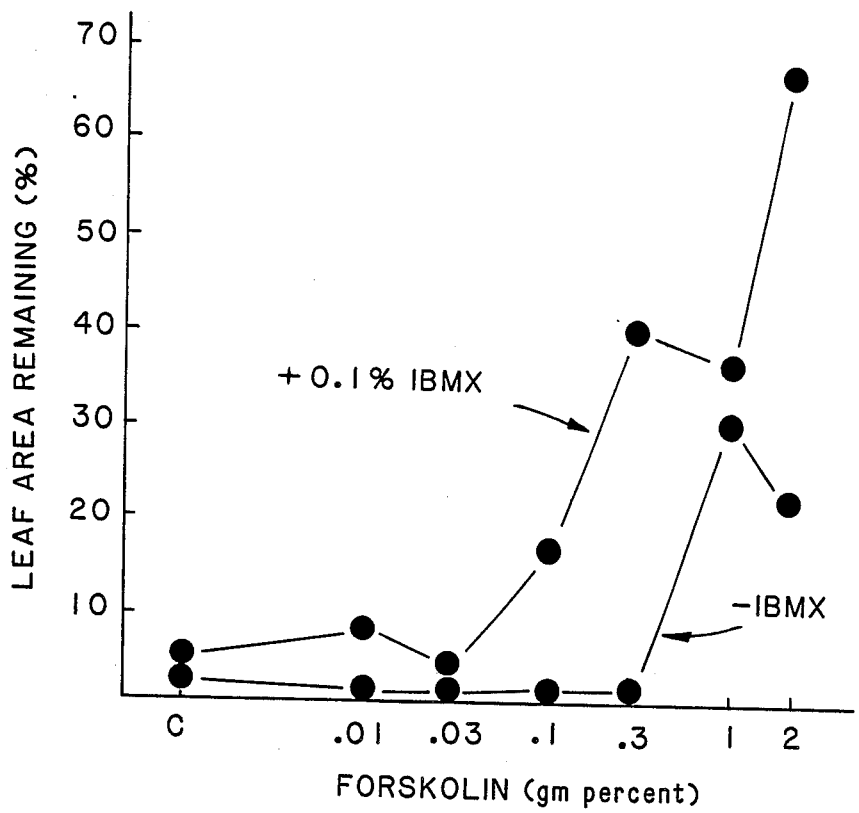
FIG. 4 shows an in vivo leaf test of a composition containing forskolin in the presence or absence of a phosphodiesterase inhibitor, IBMX.

As described previously, the diterpene forskolin is an example of a compound which directly stimulates adenylate cyclase, thereby producing cyclic AMP. FIG. 4 shows that forskolin, alone, has antifeeding activity. FIG. 4 also shows that this antifeeding activity is enhanced in the presence of (0.1%) of the PDE inhibitor IBMX.

EXAMPLE 9

In Vivo Leaf Test of a Composition Containing a cAMP Analogue

Figure 5:
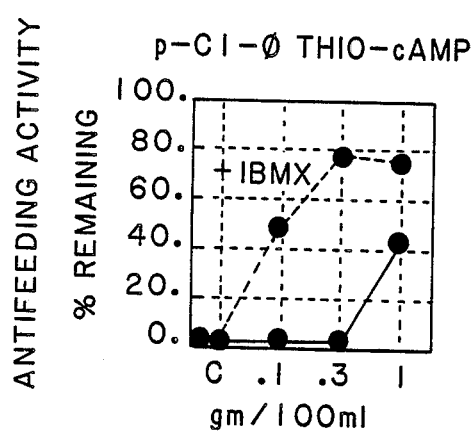
FIG. 5 shows an in vivo antifeeding activity test for the cyclic AMP analogue p-chlorophenylthiocyclic AMP in the presence or absence of IBMX.
Figure 6:
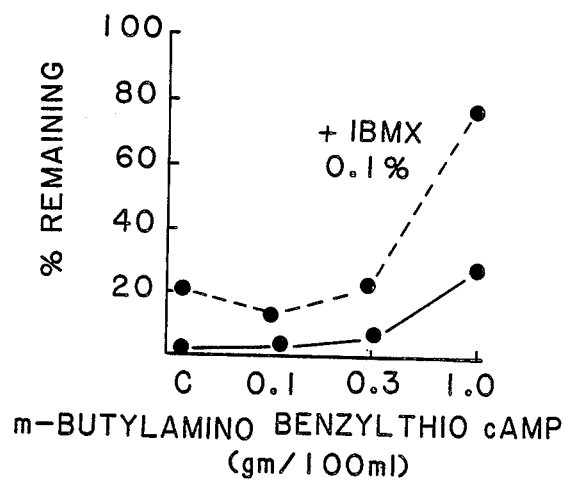
FIG. 6 shows an in vivo antifeeding activity test for leaves treated with n-butylaminobenzylthio cyclic AMP in the presence or absence of IBMX.

Two cyclic AMP analogues were tested by the leaf test. The results are shown in FIG. 5 for p-Cl-phenylthio cyclic AMP, and FIG. 6 for n-butylaminobenzylthio cyclic AMP. As can be seen, both compounds, at a concentration of 1%, showed antifeeding activity in the absence of IBMX. The activity of both compounds was increased by addition of IBMX.

Figure 7:
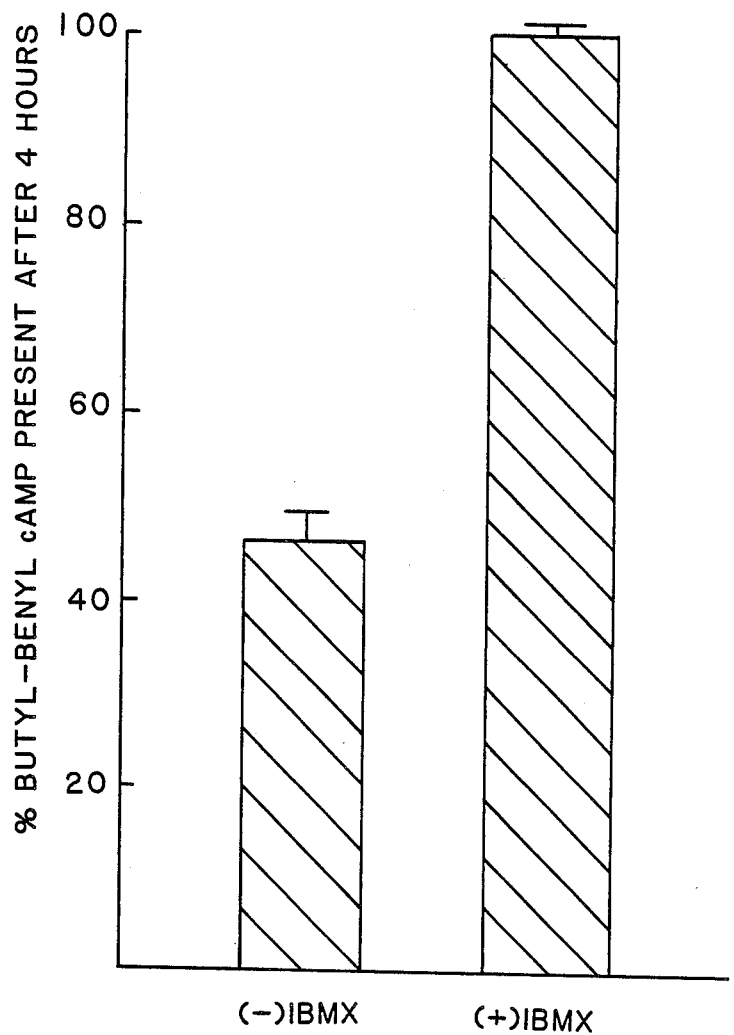
FIG. 7 shows the amount of cyclic AMP analogue butylbenzylthio cyclic AMP remaining in pest tissue in the presence or absence of IBMX.
Figure 8:
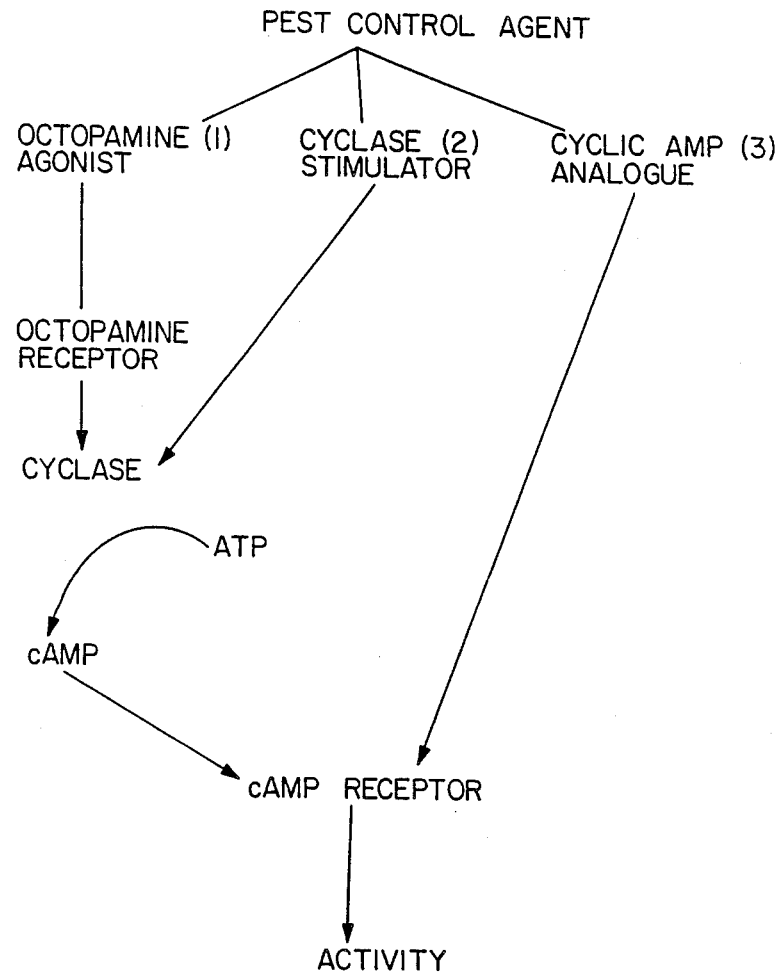
FIG. 8 illustrates the mode of action of the agents of the invention.

It has been previously shown, above, that PDE inhibition can increase the concentration of cyclic AMP in insect tissue. To further confirm the invention this example demonstrates directly that PDE inhibition can also increase the levels of cyclic AMP analogues, such as butyl-benzylthio cyclic AMP, in insect pest tissue. In order to do this, a fixed amount of butyl-benzylthio cyclci AMP was incubated in vitro for 4 hours in the presence of a tissue homogenate from tobacco hornworm nerve cord. In some tubes, IBMX (0.1 mM) was added to inhibit PDE. After the incubation, the amount of butyl-benzylthio cyclic AMP remaining was measured by protein binding assay (Brown et al., supra), using a standard curve based upon butyl-benzylthio cyclic AMP. FIG. 7 shows that addition of IBMX more than doubled the amount of butyl-benzylthio cyclic AMP present after 4 hours.

Having now fully described this invention it will be understood by those of skill in the art that the same can be performed within a wide and equivalent range of compositions, parameters, structures, modes of application, pests, formulations, and ranges without effecting the scope of the invention or or any embodiment thereof.

What is new and intended to be covered by Letters Patent of the United States is:

1. An invertebrate pest controlling composition comprising an invertebrate pest-controlling amount of a non-formamidine octopamine agonist having substantial activity toward an octopamine receptor present in an invertebrate pest and a pesticidially inert carrier.

2. The composition of claim 1 wherein the in vitro ratio $K_a^{oct}/K_a^{(1)}$ for said non-formamidine octopamine agonist is greater than 0.05.

3. The composition of claim 2 wherein said ratio is between 0.05 and 1000.

4. The composition of claim 1 which is in the form of a dust.

5. The composition of claim 1 which is in the form of a granule or pellet.

6. The composition of claim 4 or 5 wherein said carrier is selected from the group consisting of sulfur, silicon oxides, lime, gypsum, talc, pyrophyllite, bentonite, kaolins, attapulgite, and volcanic ash.

7. The composition of claim 1 which is in the form of an aerosol.

* * * * *